(12) United States Patent
Su

(10) Patent No.: US 10,932,941 B2
(45) Date of Patent: Mar. 2, 2021

(54) SEX TOY

(71) Applicant: Ching-Kuei Su, Kaohsiung (TW)

(72) Inventor: Ching-Kuei Su, Kaohsiung (TW)

( * ) Notice: Subject to any disclaimer, the term of this patent is extended or adjusted under 35 U.S.C. 154(b) by 228 days.

(21) Appl. No.: 16/124,236

(22) Filed: Sep. 7, 2018

(65) Prior Publication Data
US 2020/0078205 A1 Mar. 12, 2020

(51) Int. Cl.
*A61F 5/41* (2006.01)

(52) U.S. Cl.
CPC .......... *A61F 5/41* (2013.01); *A61F 2005/414* (2013.01)

(58) Field of Classification Search
CPC ....... A61F 5/41; A61F 2005/411; A61H 19/50
USPC ..................................... 600/38–41
See application file for complete search history.

(56) References Cited

U.S. PATENT DOCUMENTS

| 4,224,933 | A | * | 9/1980 | Reiling | ..................... A61F 5/41 600/39 |
| 6,149,580 | A | * | 11/2000 | Dabney | .................. A61H 19/00 600/38 |
| 6,736,142 | B2 | * | 5/2004 | Sanchez Gomez ... | A61F 5/0096 128/869 |
| 8,211,006 | B2 | * | 7/2012 | Park | .......................... A61F 5/41 600/39 |
| 2011/0146695 | A1 | * | 6/2011 | Taouil | ....................... A61F 5/41 128/869 |
| 2012/0215064 | A1 | * | 8/2012 | Carroll | ..................... A61F 5/41 600/39 |

* cited by examiner

*Primary Examiner* — John P Lacyk
(74) *Attorney, Agent, or Firm* — Alan D. Kamrath; Karin L. Williams; Mayer & Williams PC

(57) ABSTRACT

A sex toy includes a mounting ring body (10). The mounting ring body has a center provided with a mounting hole (11) which perforates the mounting ring body. The mounting hole of the mounting ring body has a complex slope shape. The mounting hole of the mounting ring body includes a looped restriction section (111) and an oblique tapered section (112). The mounting ring body has an outer face provided with at least one arcuate groove (12). At least one expanding ring (20) is mounted in the at least one arcuate groove of the mounting ring body.

9 Claims, 4 Drawing Sheets

SEX TOY

BACKGROUND OF THE INVENTION

1. Field of the Invention

The present invention relates to a sex toy and, more particularly, to a sex ring structure.

2. Description of the Related Art

A conventional sex ring is mounted on a male genital to provide a sex appeal. In use, the sex ring has a hole mounted on the root of the male genital. Thus, the sex ring provides a binding force on the male genital to reduce the flow back speed of the blood in the sponge of the male genital and to prolong the congestion state of the sponge of the male genital. However, the conventional sex ring has a fixed size that cannot be adjusted, thereby limiting the function of the sex ring.

BRIEF SUMMARY OF THE INVENTION

The primary objective of the present invention is to provide a sex toy that has more functions by a structural design to enhance the sex appeal.

In accordance with the present invention, there is provided a sex toy comprising a mounting ring body. The mounting ring body is a tubular body with a predetermined length. The mounting ring body has a center provided with a mounting hole which perforates the mounting ring body. The mounting hole of the mounting ring body has a complex slope shape.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
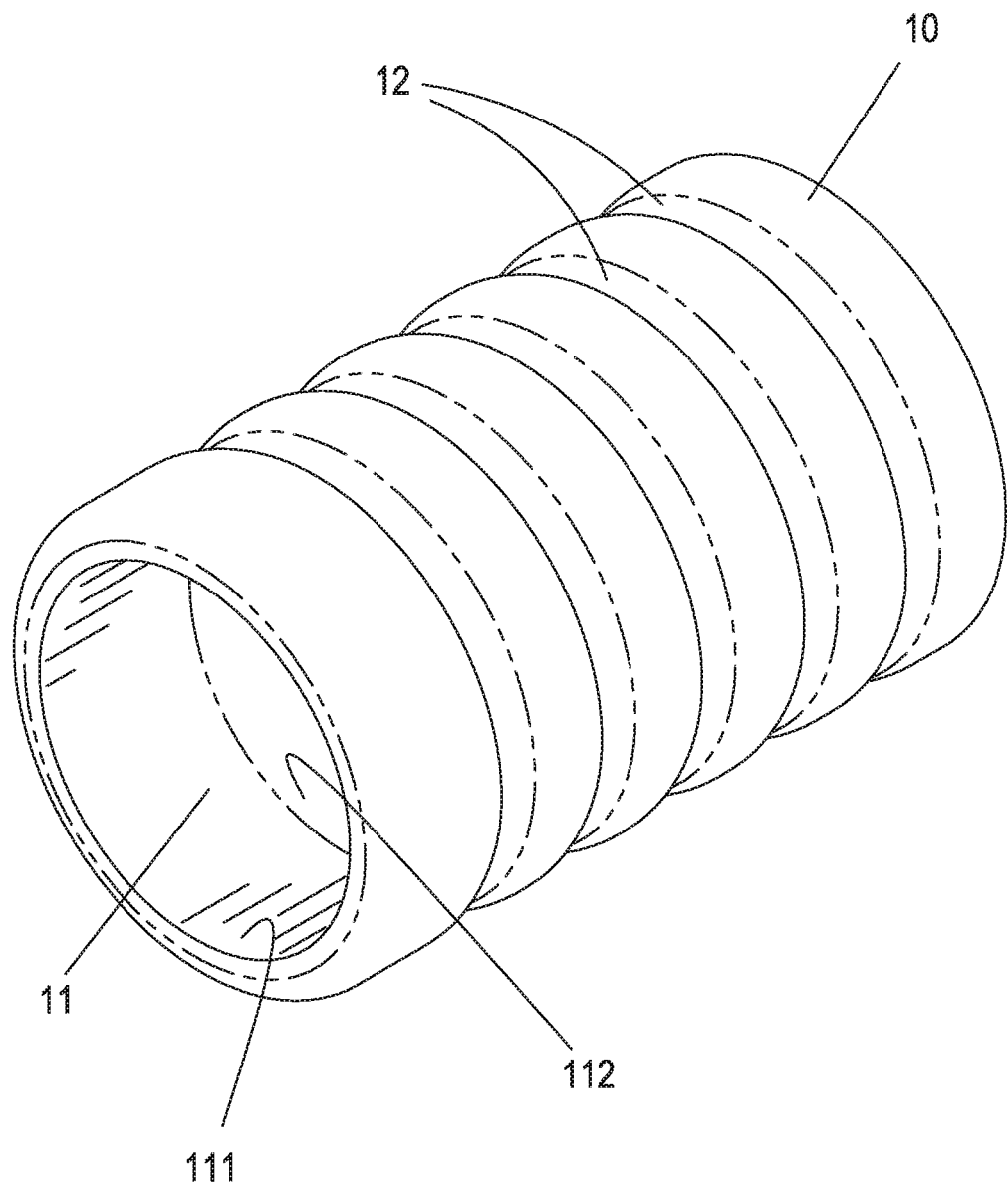
FIG. 1 is a perspective view of a sex toy in accordance with the preferred embodiment of the present invention.
Figure 2:
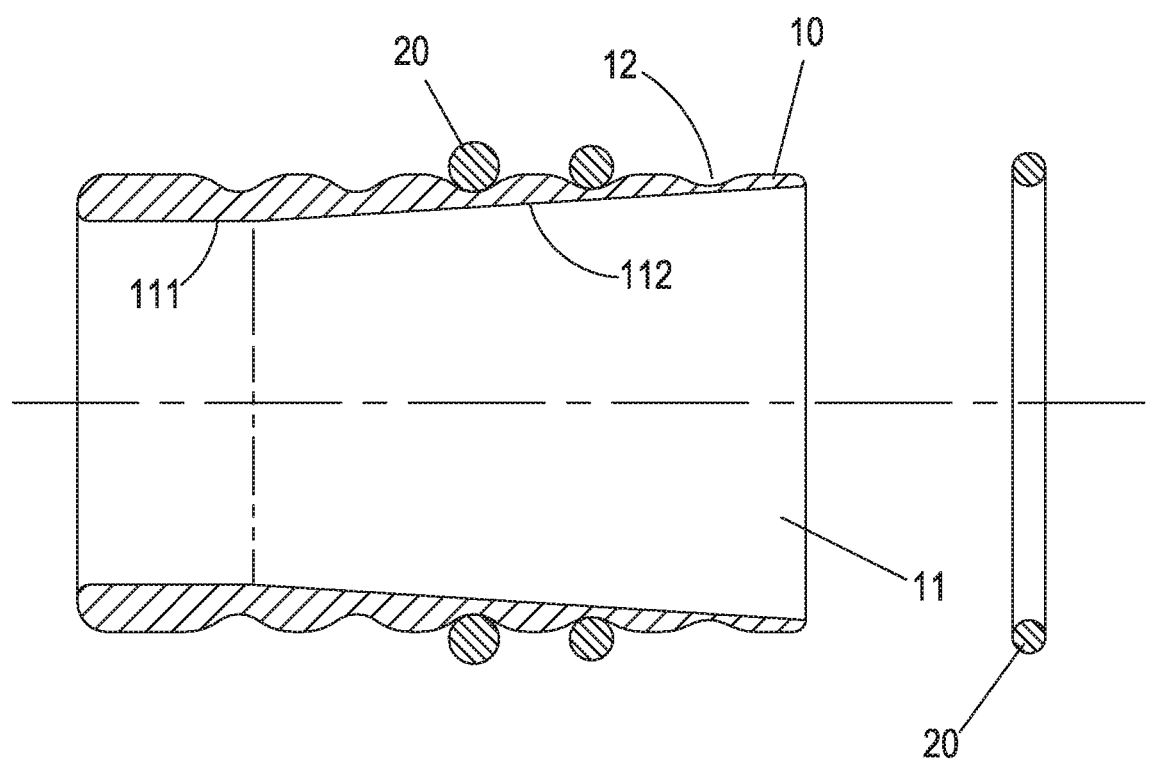
FIG. 2 is a cross-sectional view of the sex toy in accordance with the present invention.

Referring to FIGS. 1-4, a sex toy in accordance with the preferred embodiment of the present invention comprises a mounting ring body 10. The mounting ring body 10 is a tubular body with a predetermined length. The mounting ring body 10 has a center provided with a mounting hole 11 which perforates the mounting ring body 10. The mounting hole 11 of the mounting ring body 10 has a complex slope shape.

In the preferred embodiment of the present invention, the mounting hole 11 of the mounting ring body 10 includes a looped restriction section 111 and an oblique tapered section 112. The looped restriction section 111 of the mounting ring body 10 has a flat shape and has a constant diameter. The oblique tapered section 112 of the mounting ring body 10 extends forward from the looped restriction section 111 and is enlarged gradually toward a front end of the mounting ring body 10.

In the preferred embodiment of the present invention, the mounting ring body 10 has an outer face provided with at least one arcuate groove 12 having an annular shape. Preferably, the at least one arcuate groove 12 of the mounting ring body 10 has a concave and convex profile to enhance the contact effect with the user. Thus, the concave and convex configuration of the at least one arcuate groove 12 produces an exciting effect to a female genital, thereby enhancing the sex feeling.

In the preferred embodiment of the present invention, the sex toy further comprises at least one expanding ring 20 mounted on the mounting ring body 10 and retained in the at least one arcuate groove 12 of the mounting ring body 10. Thus, the at least one expanding ring 20 increases the diameter of the mounting ring body 10 so as to enhance the exciting effect.

In the preferred embodiment of the present invention, the at least one expanding ring 20 has a cross-section with at least one size according to the user's practical requirement.

In the preferred embodiment of the present invention, the mounting ring body 10 has different models with smooth angle variation to provide a comfortable sensation to the user when touching the user's skin.

Figure 3:
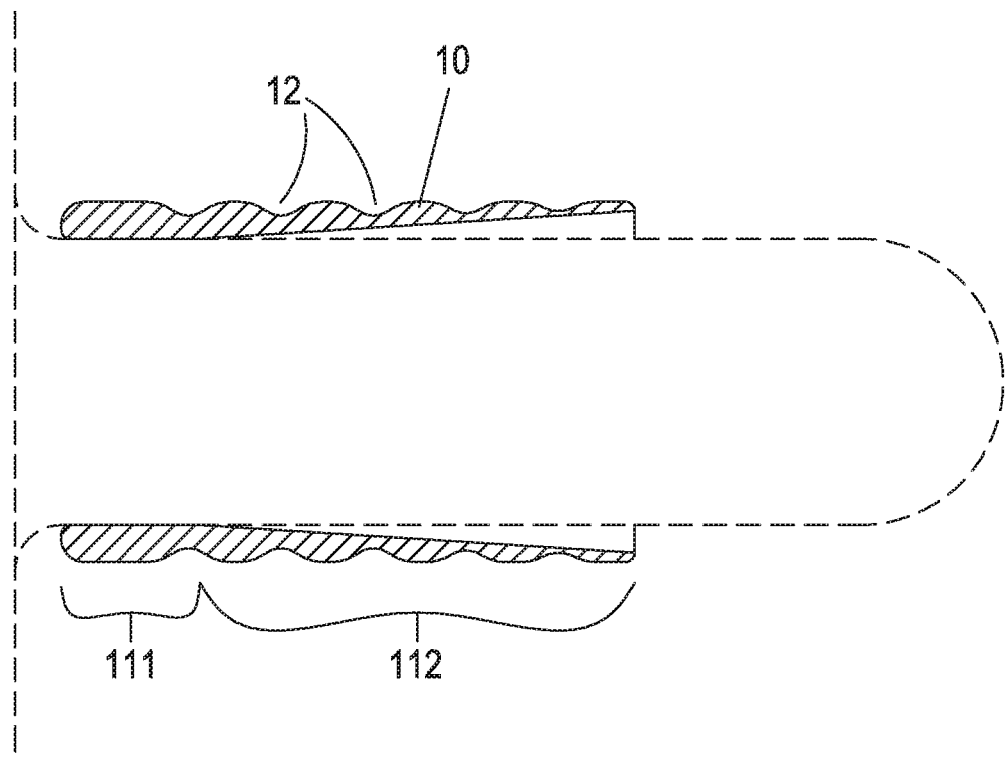
FIG. 3 is a cross-sectional view showing usage of the sex toy in accordance with the preferred embodiment of the present invention.
Figure 4:
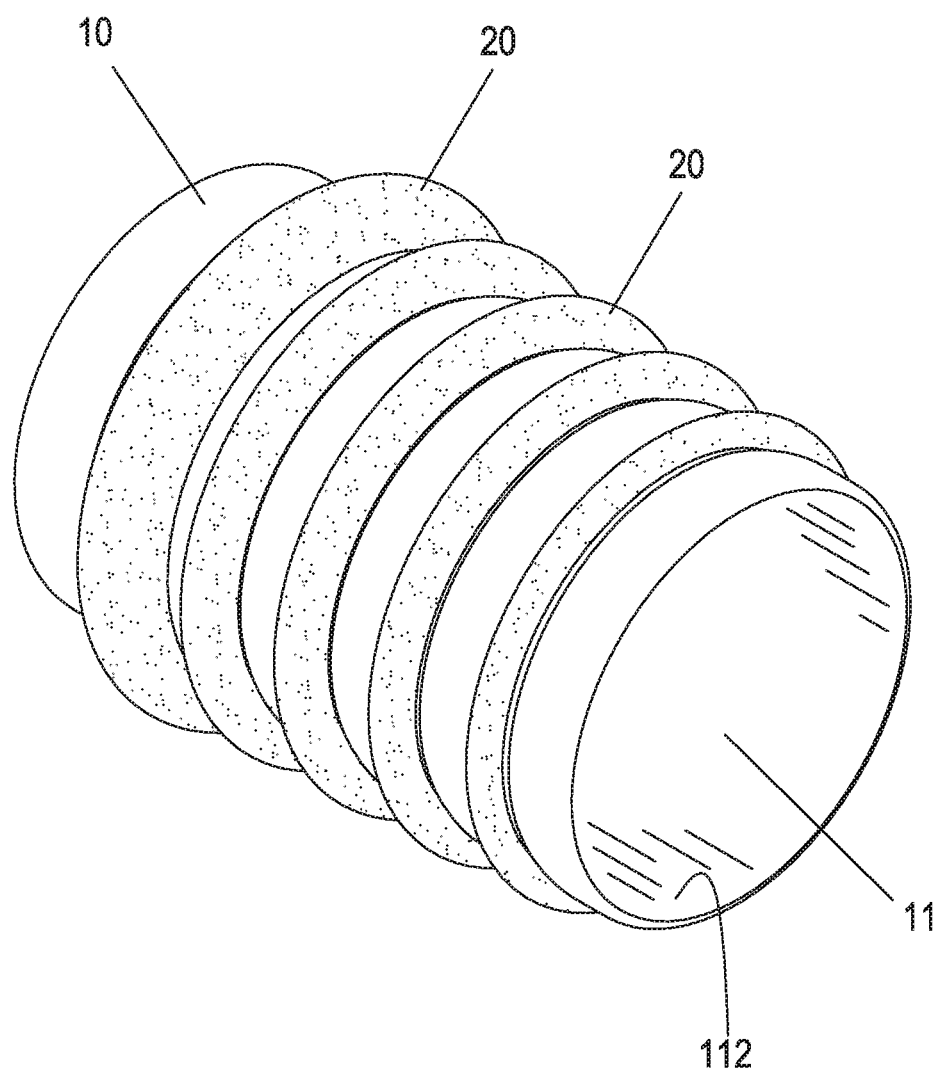
FIG. 4 is a perspective view of a sex toy in accordance with another preferred embodiment of the present invention.

As shown in FIG. 3, when a male genital is inserted into the mounting hole 11 of the mounting ring body 10, the looped restriction section 111 of the mounting ring body 10 presses the root of the male genital and provides a binding force on the male genital, to refrain and prevent the blood in the sponge of the male genital from flowing back, such that the male genital is kept at a stiff congested state.

Accordingly, the at least one arcuate groove 12 is formed in the outer face of the mounting ring body 10 and has a concave and convex design to enhance the function of the mounting ring body 10. In addition, the at least one expanding ring 20 is mounted on the mounting ring body 10 to enhance the exciting effect and sex appeal.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the scope of the invention.

The invention claimed is:

1. A sex toy comprising:
   a mounting ring body;
   wherein:
   the mounting ring body is a tubular body with a predetermined length;
   the mounting ring body has a center provided with a mounting hole which perforates the mounting ring body;
   the mounting hole of the mounting ring body includes a looped restriction section and an oblique tapered section;
   the looped restriction section of the mounting ring body has a constant diameter;
   the oblique tapered section of the mounting ring body extends forward from the looped restriction section and is enlarged gradually toward a front end of the mounting ring body; and
   the mounting ring body has an outer face provided with at least one arcuate groove.

2. The sex toy of claim 1, further comprising:
at least one expanding ring mounted on the mounting ring body and retained in the at least one arcuate groove of the mounting ring body.

3. The sex toy of claim 2, wherein the at least one expanding ring has a diameter more than that of the mounting ring body.

4. The sex toy of claim 2, wherein the at least one expanding ring protrudes outward from the mounting ring body.

5. The sex toy of claim 2, wherein the at least one expanding ring is partially received in the at least one arcuate groove of the mounting ring body and partially protrudes outward from the at least one arcuate groove of the mounting ring body.

6. The sex toy of claim 2, wherein the at least one expanding ring has an endless shape.

7. The sex toy of claim 1, wherein the at least one arcuate groove of the mounting ring body surrounds the looped restriction section.

8. The sex toy of claim 1, wherein the at least one arcuate groove of the mounting ring body surrounds the oblique tapered section.

9. The sex toy of claim 1, wherein the looped restriction section is connected with the oblique tapered section.

\* \* \* \* \*